United States Patent [19]

Gavish

[11] Patent Number: 4,580,574

[45] Date of Patent: Apr. 8, 1986

[54] METHOD AND DEVICE FOR NON-INVASIVELY MONITORING THE INSTANTANEOUS FLUCTUATIONS IN THE VISCOELASTIC-RELATED PROPERTIES OF A LIVING TISSUE

[76] Inventor: Benjamin Gavish, 65 Yasmin Street, Schehuna Alef, Mevasseret Zion Jerusalem 90805, Israel

[21] Appl. No.: 636,010

[22] Filed: Jul. 30, 1984

[30] Foreign Application Priority Data

Aug. 12, 1983 [IL] Israel ........................................ 69471

[51] Int. Cl.$^4$ ............................................. A61B 10/00
[52] U.S. Cl. .................................... 128/660; 128/774; 73/589
[58] Field of Search ............................... 128/774–778, 128/660–661, 663; 73/586, 589, 597–600

[56] References Cited

U.S. PATENT DOCUMENTS

| | | | |
|---|---|---|---|
| 3,847,141 | 11/1974 | Hoop | 128/660 |
| 4,250,894 | 2/1981 | Frei et al. | 128/774 |
| 4,297,884 | 11/1981 | Leveque et al. | 128/774 X |
| 4,361,154 | 11/1982 | Pratt, Jr. | 128/774 X |
| 4,414,984 | 11/1983 | Zarudiansky | 128/774 |

OTHER PUBLICATIONS

Chung, J. K. et al., "A New Diagnostic Technique for the Evaluation of Prosthetic Fixation", Conf: IEEE 1979 Frontiers of Engr. in Health, Denver, Colo., Oct. 6–7, 1979.

Sollish, B., "A Device for Measuring UTS Propagation Velocity in Tissue", Reprint of U.T.S. Tissue Characterization II, M. Linzer, ed., NBS Spec. Publ. 525 (U.S. Govt. GPO, Wash. DC, 1979).

Primary Examiner—Kyle L. Howell
Assistant Examiner—Francis J. Jaworski
Attorney, Agent, or Firm—Stevens, Davis, Miller & Mosher

[57] ABSTRACT

The invention provides an ultrasonic device for continuously and noninvasively monitoring instantaneous fluctuations in viscoelastic-related properties of tissue comprising a pair of substantially parallel spaced-apart piezoelectric transducers having a gap therebetween and adapted to bracket and come in direct contact with living tissue inserted in the gap between the transducers, at least one of the transducers being adjustable with respect to the other transducer whereby the distance between the transducers is adjustable to enable insertion and clamping of a segment of living tissue therein. The invention also provides a method for continuously and noninvasively monitoring instantaneous fluctuations in viscoelastic-related properties of a tissue with high resolution utilizing such a device.

5 Claims, 7 Drawing Figures

METHOD AND DEVICE FOR NON-INVASIVELY MONITORING THE INSTANTANEOUS FLUCTUATIONS IN THE VISCOELASTIC-RELATED PROPERTIES OF A LIVING TISSUE

BACKGROUND OF THE INVENTION

1. Field of the Invention

The present invention relates to a device and method for monitoring, noninvasively and in a nonperturbating way, dynamic variations in viscoelastic-related properties of a tissue. More particularly, the present invention relates to an ultrasonic device that monitors continuously, noninvasively and without perturbing the blood flow, small-amplitude instantaneous fluctuations in the velocity and absorption of ultrasonic waves in a living tissue, caused by the blood microcirculatory system and to a method for the use thereof.

2. Discussion of the Prior Art

The supply of oxygen and nutrients to the body's tissues is mediated by a complex system of small blood vessels, i.e. microvessels, having diameters ranging from 0.005 to 0.5 mm. This so-called microcirculatory system modulates the distribution of blood by utilizing a sophisticated system of microscopic muscles, which are subject to neural control. The muscles change the diameter of some of the blood vessels (arterioles) and connect/disconnect the blood supply to the capillaries, causing the volume of fluids and its red blood cell content (hematocrit) to fluctuate in time (Zweifach, B. W. (1961)—Functional Behaviour of the Microcirculation, Charles Thomas, Springfield).

The resulting fluctuations in the blood supply and the related variations in the diameter of some of the microvessels are called vasomotion. Vasomotion is subject to neural control and its dynamic characteristics are significantly altered in case of some cardiovascular diseases including diabetes, hypertension, arteriosclerosis and related disorders [Davies, E., S. Ben-Hador and J. Landau (1962) 2nd Europ. Conf. Microcirculation, Pavia, Bibl. anat. 4, 195-200, Karger, Basel/New York (1964)].

Accumulating evidence supports the idea that vasomotion propels the blood and thus maintains its fluidity (Schmid-Schönbein, H. (1981) Interaction of vasomotion and blood rheology in haemodynamics. In: Clinical Aspects of Blood Viscosity and Cell Deformability. Eds. Lowe, G. D. O., Barbenel, J. C., Springer Verleg, pp. 49-67). This is because blood viscosity, which is an important clinical parameter, increases strongly at small velocity gradients.

Drugs, anaesthetics and emotional stress induce vasodilation or vasoconstriction of the microvessels, which is favorable in some cases and unfavorable and often harmful in others, e.g. overloading the heart by decreasing the peripheral resistance in case of massive vasodilation and causing insufficiency of blood supply to tissues in cases of prolonged vasoconstriction.

In addition to the above "active" and relatively slow changes in the microcirculatory system, some microvessels respond "passively" to the pulse pressure by changing their volume. The response involves the viscoelastic properties of the microvessel wall, which undergo variations in case of some cardiovascular diseases, e.g. in arteriosclerosis, and are strongly nonlinear as functions of the phase of the vessel i.e. being dilated, constricted or relaxed (Wiederheilm, C.A. (1964), Viscoelastic properties of relaxed and constricted arteriolar walls. 3rd European Conference on Microcirculation, Jerusalem, Bibl. anat. 7, 346-352 Karger, Basel/New York 1965). The pattern displayed by these volume fluctuations reflect the capability of the microcirculatory system to follow the pressure pulse, as generated at the heart and propagated along the circulation pathway.

The following can thus be concluded: (a) A wide range of clinical situations are associated with the dynamic behavior of the microcirculatory system. (b) Microcirculation dynamics involves variations in the volume and the viscoelastic properties of some of the tissue components. (c) One can infer from (a) & (b) that monitoring, at real time, physical parameters, which are related to fluctuations in the viscoelastic properties of a tissue, i.e. the sum of the volume-weighted contributions of its components, will prove to be extremely valuable for clinical medicine and diagnosis.

What is therefore needed is a method for continuous, noninvasive and highly-sensitive monitoring of fluctuations in viscoelastic-related properties of a tissue.

SUMMARY OF THE INVENTION

With this background in mind, the present invention provides an ultrasonic device for continuously, nonperturbingly and noninvasively monitoring of instantaneous fluctuations in the velocity and/or absorption of ultrasound in a bulk of a tissue. These quantities are generally related to the volume-weighted viscoelastic properties of the tested medium. The device comprises a pair of substantially parallel spaced apart piezoelectric transducers, having a gap therebetween and adapted to bracket and come in direct contact with living tissue inserted in said gap between said transducers at least one of said transducers being adjustable with respect to the other transducer whereby the distance between said transducers is adjustable to enable insertion and clamping of a segment of living tissue therein, so that the transducers are in direct contact with the tissue.

According to the present invention, there is also provided a method for continuously, nonperturbingly and noninvasively monitoring instantaneous fluctuations in viscoelastic related properties of a tissue in a very high resolution comprising:

providing a pair of substantially parallel spaced apart piezoelectric transducers having a gap therebetween, at least one of said transducers being adjustable with respect to the other; inserting a segment of living tissue into said gap between said spaced apart transducers; adjusting the distance between said transducers so as to bring both transducers in direct contact with said living tissue; generating continuous ultrasonic waves using one of the transducers; propagating said waves through said tissue undergoing multiple reflections between the transducers; monitoring the signal as generated by the other transducer; and analyzing the resulting signals.

In a preferred embodiment of the method of the present invention, as described hereinafter, a tunable frequency source is utilized at a sweep mode for probing instantaneous displacements in the resulting peak structure.

That the viscoelastic properties of liquids in general can be elucidated from the measurements of the velocity and absorption of ultrasonic waves in these media can be seen from the literature [e.g., Litovitz, T. A. & C. M. Davies (1968) Structural and shear relaxation in liquids, in: Physical Acoustics, Ed. W. P. Mason, Vol. 11/A (Academic Press, New York) 281-349].

Thus the sound velocity C (measured at frequency f) and the density $\rho$ of a liquid are related to its bulk compressibility $\beta$ by the following relation:

$$\beta = 1/\rho C^2$$

The sound absorption coefficient $\alpha$ is the reciprocal value of the distance over which the pressure amplitude of a longitudinal sound wave decays by a factor of e. For practical cases, in the so-called "hydrodynamic limit", one can show $$\alpha = (2\pi^2 f^2/\rho C^3)[4/3\eta_s + \eta_v] \quad (2)$$

where $\eta_s$ is the "shear viscosity" (as measured by flow viscometers) and $\eta_v$ is the "volume viscosity". For most of the liquids $\eta_s$ & $\eta_v$ are in the same order of magnitude, thus $\alpha$ gives a measure for the bulk viscosity at a given frequency, wherein C and $\alpha$ are the viscoelastic-related parameters.

Thus it is known that high-precision measurements of C and $\alpha$ for small volume liquid samples can be achieved by using the resonator method that was originally developed by F. Eggers in 1967 and was applied successfully to liquids [see, e.g. Eggers, F. and Th. Funck (1973) Ultrasonic measurements with milliliter liquid samples in the 0.5-100 MHz range. Rev. Sci. Instrum. 44 969-977].

It has however heretofor neither been taught nor suggested to use a modified version of the resonator method for dynamic, continuous and noninvasive measurements of instantaneous fluctuations of C and $\alpha$ in a tissue in vivo. This concept is first suggested herein despite the widefelt need for such a device and method as explained hereinbefore.

Furthermore, there exist substantial differences and dissimilarities between the conventional ultrasonic resonator (CUR) as described in the literature (Eggers & Funck, 1973, ibid) and the device of the present invention in structure, performance and the nature of the measured quantities as follows:

(a) Structural: The CUR consists of a cell or container that encloses a liquid sample. Objects, if immersed in the liquid, are generally not in direct contact with the crystals, which establish part of the cell walls. In the present device the transducers are adapted to bracket and are in direct contact with a part of living tissue. Thus, the present device does not include a cell or a container, the medium here is not a liquid or a liquid containing immersed objects, but a living tissue with which the transducers are in direct contact.

(b) Performance and Measured Quantities: The output of the CUR is considered as meaningful when a stable equilibrium is reached. Thus, the acoustic properties of the sample are time-independent. This requires excellent stability in temperature (within 0.001° C., see Eggers & Funck, 1973). Temperature fluctuations are considered as the main, difficult to control, source of experimental errors. Here the performance involves a system which is far from thermal, chemical or mechanical equilibrium. The time dependence of the acoustic properties of the tissue is the relevant measurable parameter. The equilibrium, or time averaged properties are less important and not too meaningful. Thus, what is considered as information in the present device is considered as noise or error in the CUR. The specific application of the device for probing the fluctuations in the viscoelastic properties of blood microcirculatory system is novel and there is not available or known today any noninvasive method that can directly probe these properties in vivo.

Thus the known state of art in, noninvasive, in-vivo, applications of ultrasound for clinical measurements can be divided into three main categories:

(a) Methods of measuring blood flow using Doppler effect: This method is applied for large blood vessels, as arteries [Taylor, D. & J. Whamond (editors) (1977) Non-invasive clinical measurements. University Park Press, Baltimore] and gives information about the velocity field, but not about viscoelastic properties (b) Ultrasonic imaging: Using a computerized "time-of-flight" analysis of ultrasonic pulses, one can reconstruct an image which gives information about the boundaries between regions possessing different acoustic impedances (a device of this kind is manufactured, for example, by Elscint, Israel). This application, however, does not involve the aspects which are essential for the present invention. Actually, the large difference between the acoustic impedance of the blood vessel and its surrounding tissue makes this method insensitive to the properties of the blood itself, and (c) Ultrasonic tissue characterization: The title stands for the efforts to characterize a whole tissue by the absolute values of the velocity and absorption of ultrasonic waves and their frequency dispersion, in the tissue. However, the subject is still on the level of basic research mostly in vitro, and with no applicable conclusions for in vivo systems. The present approach is radically different by relating instantaneous fluctuations in acoustic properties to the in vivo viscoelastic-related properties of a small part of a tissue, which presumably generates these fluctuations. Here microcirculation dynamics are characterized and not the static acoustic properties of the tissue as a whole.

It should be mentioned that both ultrasonic Doppler and imaging techniques are not informative concerning blood vessels having diameters smaller than about 0.5 mm. The present method is favourably applied to tissues containing structural elements that generate fluctuations in C and $\alpha$ having dimensions ranging from atomic sizes up to about 0.5 mm, which is the limit of resolution of other diagnostically-applied imaging techniques like NMR. All Doppler-based techniques require a well-defined orientation to the measured blood vessels and thus cannot be applied to a nearly-random three-dimensional network of microvessels in the bulk of a tissue, to which the present method is applicable; (using light, laser Doppler flowmeter can measure the flow in the skin capillaries which establish a two dimensional array).

Since both C and $\alpha$ are weighted by the volume of the various tissue components, one should expect that in some situations, part of the measured fluctuations might be attributable to relative volume fluctuations of the tissue components.

BRIEF DESCRIPTION OF THE DRAWINGS

While the invention will now be described in connection with certain preferred embodiments with reference to the following illustrative figures so that it may be more fully understood, it is stressed that the particulars shown and described are by way of example and for purposes of illustrative discussion only and are presented in the cause of providing what is believed to be the most useful and readily understood description of the principles and conceptual aspects of the invention. In this regard no attempt is made to show structural details of the devices of the invention and their component parts in more detail than is necessary for a fundamental understanding of the invention, the description taken with the drawing making apparent to those skilled in the art how the several forms of the invention may be embodied in practice.

In the drawings.

DETAILED DISCUSSION OF THE PREFERRED EMBODIMENTS

Figure 1:
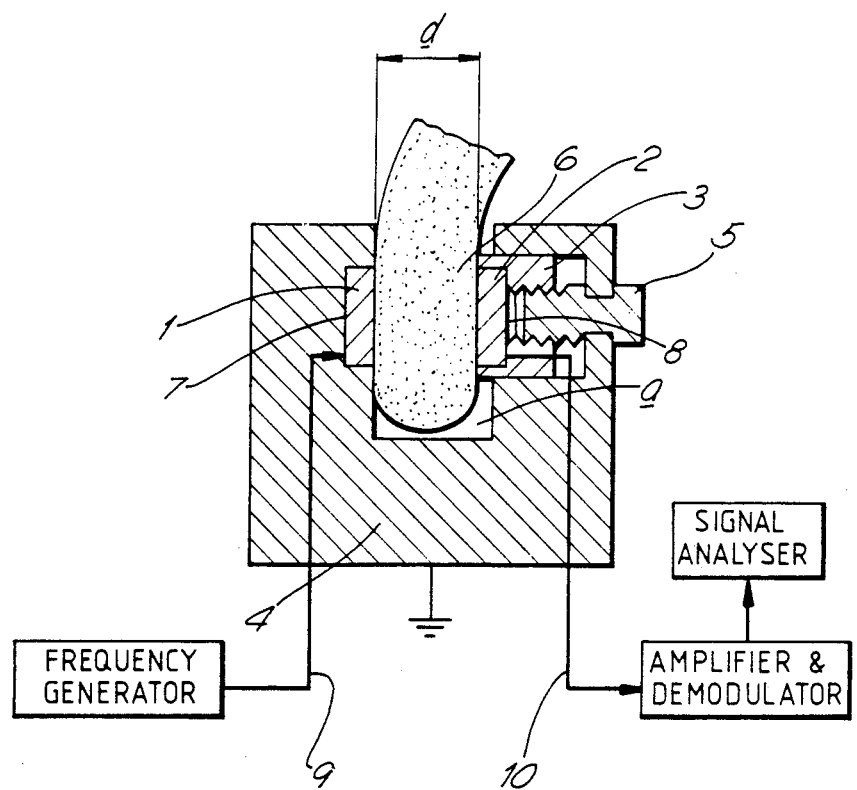
FIG. 1 is a cross-sectional view showing the device according to the invention clamped on a living tissue and electrically connected to input and output devices.

As seen, on a mount 4 there is rigidly affixed a piezoelectric transducer 1 and across a gap a in the mount 4, there is held a piezoelectric transducer 2 by means of an insert 3 adjustably slidable in the mount 4 by means of a manipulatable screw 5.

The distance d between the transducers 1 and 2 is variable so that when a tip of a soft tissue 6 is inserted into the gap a between the transducers, an intimate contact between the tissue and the transducers can be obtained merely by decreasing the distance d therebetween.

Optionally, the mount 4 may be provided with additional, known per-se, adjusting means so as to facilitate the fine adjustment of the required parallelism between the two transducers for all ranges of the d values. The exposed surfaces of the transducers which are in contact with the tissue, as well as the mounts or holders (if metallic) are grounded. The opposite side surfaces of the transducers serve as the input/output electrodes, respectively, electrodes 7 and 8. Two coaxial cables 9 and 10, respectively connect these electrodes to a frequency generator at the input and to an amplifier and a demodulator at the output and in turn to a signal analyser as shown. Each of the transducers can, in fact, serve as an input or output.

In operation, the device is superimposed on a tip of a tissue such as an earlobe and is fixed in place by an attached accessory, which is specific to the tested organ (not shown in FIG. 1). During this time, the electronic parts of the system are working. Using, e.g., an adjusting screw, the gap between the transducers is diminished. The signal analyser releases two signals during this time, $V_{01}$ or $V_{02}$ which are displayed on a screen in the sweep mode (see FIG. 4). Some jelly should advantageously be applied to the crystals to improve the acoustic matching.

Figure 2:
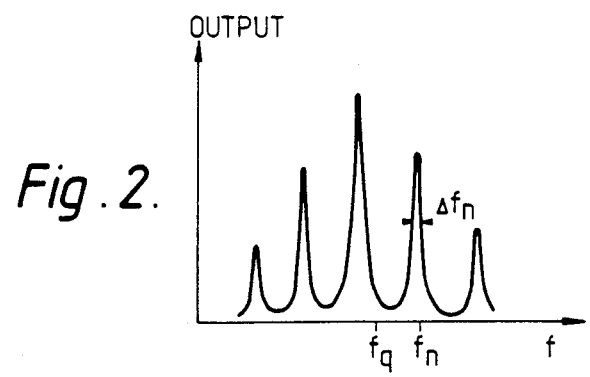
FIGS. 2, 3 and 4 schematically show in graph form various outputs (voltages) of the device.

Applying at the input a sine-wave voltage, having the frequency f, the demodulated output of the device is a voltage which possesses, as a function of f, a peak structure that is mostly pronounced around $f_Q$, $3f_Q$, $5f_Q$... where $f_Q$ is the resonance frequency of the crystals (FIG. 2). It can be shown that for the $n^{th}$ peak, which is centered around $f_n$ and possesses a half-power-band $\Delta f_n + a$, the sound velocity C and the sound absorption $\alpha$ of the tested medium at $f_n$ are related to $f_n$ and $\Delta f_n$ as follows:

$$a\lambda_n/\pi = \Delta f_n/f_n \quad C \sim \lambda_n f_n \qquad (3)$$

where $\lambda_n = 2d/n$ is the wavelength, and a is a constant contribution of the device itself, being filled, e.g., with nonabsorbing material (Eggers & Funck, 1973, ibid).

Using Eqs. (1)–(3) we find $$\Delta f_n \sim (2\pi/\rho\lambda_n^2)\eta^* \qquad (4)$$

where $\eta^* = (4/3)\eta_s + \eta_v$ is a combined "viscosity". In the conventional use of this so-called "resonator method" a frequency sweep, if performed, gives data (FIG. 2) that are analysed manually or semi-automatically for obtaining $\alpha$ and C. During the measurements an excellent temperature stabilization is required ($\pm 0.001°$ C.) (Eggers & Funck, 1973, ibid). In the present invention of interest is the relative fluctuations of $\alpha$ and/or C, that stem from internal processes, on real time. If the time scale of these processes is much longer than the period of a single frequency sweep, then $\alpha$ and C are well-defined instantaneously. Assuming that $\rho$ is a constant, we find:

$$\delta\eta^*/\eta^* = \delta(\Delta f_n)/\Delta f_n \quad \delta C/C = \delta f_n/f_n \qquad (5)$$

Figure 3:
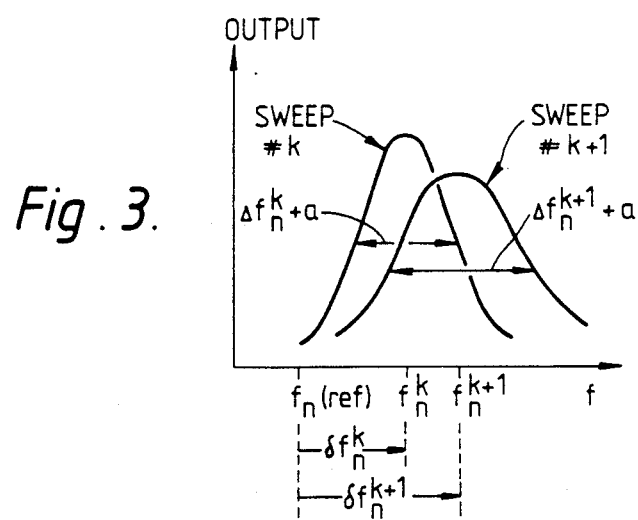

An example of a possible way of simultaneous measurement of $f_n$ and $\Delta f_n$ as functions of time is illustrated in FIG. 3. Solid sweep curve #K and #K+1 describe the structure of the nth resonant peak, as obtained by performing two frequency sweeps at times $K\Delta t$ and $(K+1)\Delta t$ respectively, where $K = 1, 2, 3, \ldots$ and $\Delta t$ is a constant time interval. The corresponding peak locations are $f_n^k$ and $f_n^{k+1}$ and the widths of the resonance curves are $\Delta f_n^k + a$ and $\Delta f_n^{k+1} + a$, in which a is related to the contribution of the device (without the sample) to the total width of the curve. Taking $f_n$ (ref) to be an arbitrary reference for frequency measurement of a peak location, $\Sigma f_n^k$ and $\Sigma f_n^{k+1}$ are the related fluctuations in the peak location. Consider the case of a heterogeneous system in which the $i^{th}$ component that occupies the volume fraction $x_i$ possesses $C_i$ & $\alpha_i$ the observed value of the ultrasonic velocity will take the form $$C = \Sigma_i x_i C_i \qquad (6)$$

and the relative value of an instantaneous fluctuation in is given as follows:

$$\delta f_n/f_n = \delta C/\bar{C} = \Sigma_i (\delta x_i/x_i + \delta C_i/C_i) x_i (C_i/\bar{C}) \qquad (7)$$

where $\bar{C}$ is the average value of C. Similar expressions to Eqs. (6) to (7) hold, respectively, for $\eta^*$ and $\delta\eta^*/\eta^*$ (or approximately for $\alpha$ and $\delta\alpha/\alpha$). Eq. (7) shows that the measured parameters i.e. $\delta(\Delta f_n)$ and $\delta f_n$ are related to fluctuations in volume fraction and the viscoelastic properties of the system components. The measurements are mostly meaningful if the size of the various components is smaller than the ultrasonic wavelength which is about 0.5 mm.

Figure 4:
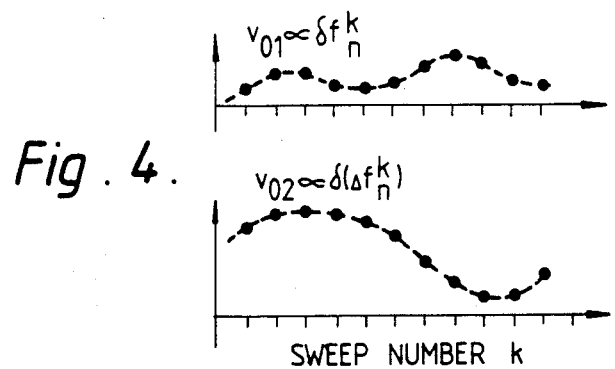

After amplifying and demodulating the output, a fast and on-line data analysis is applied. The final output is shown in FIG. 4: At the end of each sweep the signal analyser releases two signals $V_{01} \propto f_n - f_n(ref) = \delta f_n$, $V_{02} \propto \Delta f_n - \Delta f_n(ref) = \delta(\Delta f_n)$ where $f_n(ref)$ and $\Delta f_n(ref)$ are adjustable references. It is important to note that $\delta f_n/f_n$ & $\delta(\Delta f_n)/\Delta f_n$ are independent of the amplitude of the input/output of the device and the gap d and thus characterize the tissue itself.

Simple estimations based on literature data suggest that the dominant contribution to $\delta C/\overline{C}$ in the microcirculatory system stems from its fluid content. Thus, we expect that $\delta f_n \propto \delta X$ where $\delta X$ is the fluctuation in the volume fraction of fluids; on the other hand, since the fluids give merely a small contribution to the tissue absorption, the main contribution to $\delta(\Delta f_n)$ stems from the microvessels walls that changed their viscosity appreciably during vasomotion, but keep their volume unchanged (Widerhielm, 1964, ibid). Thus $\delta(\Delta f_n) \propto \delta\eta^*$ where $\delta\eta^*$ corresponds to the microvessels walls.

Figure 5:
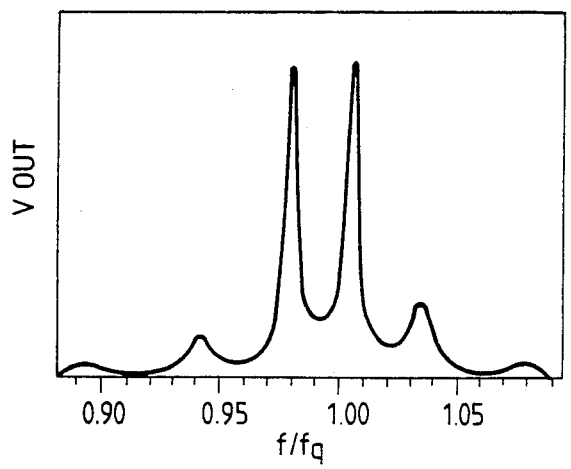
FIGS. 5, 6 and 7 are graphic presentations of experimental results in vivo using the device and method of the present invention on a human subject.

A prototype of this device has been constructed and the preliminary results in vivo were satisfactory. Some of the results of said invention during in vivo testing were as follows:

(a) The output of the device, when applying to a soft tissue in vivo displayed the expected resonances of a homogeneous medium as shown in FIG. 5 in which the output of the device is plotted as a function of frequency f in the units of the resonance frequency $f_Q$ of the transducers.

Figure 6:
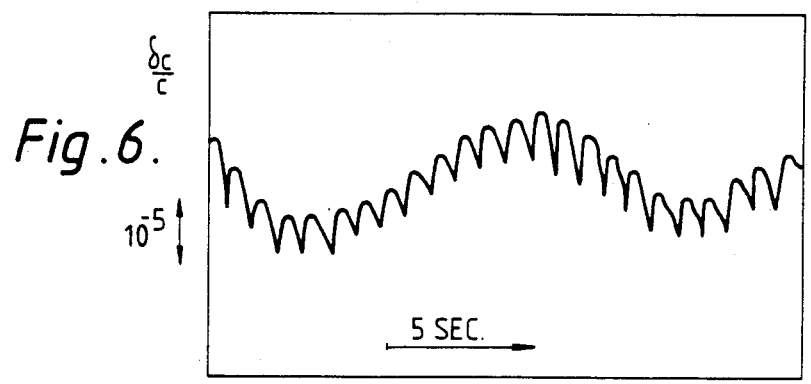

(b) On monitoring $\delta f_n$ the output was found to contain a fast component that possessed the heart-beat cycle and a slow component with the output being expressed as the relative change in the sound velocity as a function of time as shown in FIG. 6.

Figure 7:
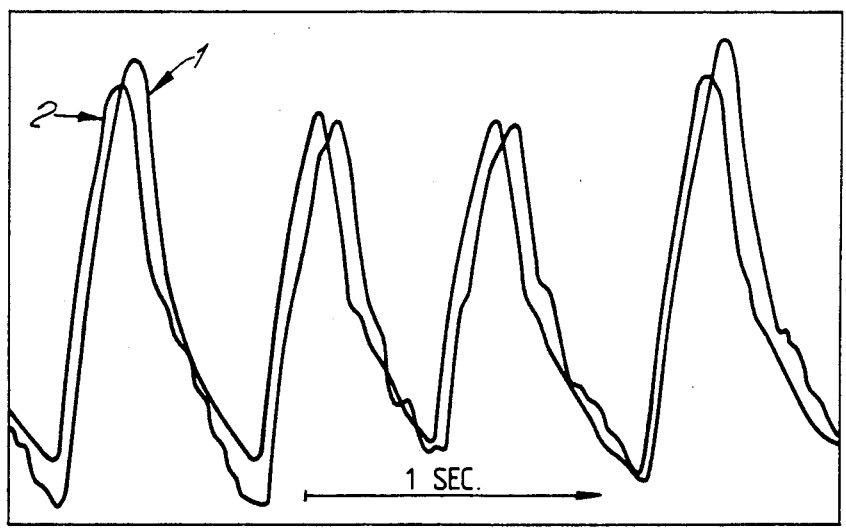

FIG. 7 shows a simultaneous recording of $\delta C/C$ (trace 1) measured at the earlobe and the aortic pressure (trace 2) measured by an invasive method during a heart catheterization, in case where the microvessels were supposed to be dilated. Since volume changes in elastic vessels follow pressure variations, the close similarity between the traces confirms our estimation concerning the dominant contribution of $\delta f_n$ from the tissue fluids.

The resolution of $\delta C/C$ was about $10^{-6}$ in FIG. 6, however the device is capable of showing the finer structure of signals as seen in FIG. 7, in which the noise level was smaller than the thickness of the trace line.

(c) These features were easily reproducible.

(d) The resonance pattern itself was extremely stable during 5 hours of a test.

(e) Wearing the device for 5 hours did not cause any inconvenience.

(f) The power of the ultrasonic radiation that was used in this device ($<1$ mW/cm$^2$) is smaller by two orders of magnitude than the power used for the conventional clinical applications of ultrasound (imaging & Doppler).

Referring to the capability of the device to monitor fluctuations in the fluid volume on the microcirculatory level, its performance should be compared to a family of existing devices, plethysmographs, that measure related parameters. Most of them—strain gauge, pneumatic, impedance, hydraulic and oculo-plethysmographs are mounted on organs that contain large blood vessels as well, thus the contribution of the microvessels cannot be identified. Photoplethysmographs selectively monitor the concentration of hemoglobin in a tissue, which might be proportional to the blood volume. Its output, however, is irreproducible and cannot be calibrated [see evaluations of various plethysmographs in Kempczinski, R. F. and J. S. T. Yao (1982) Practical Noninvasive Vascular Diagnosis, Year Book Medical Publishers, Chicago]. Recently, A. Hoeks and D. Phillips have independently developed ultrasonic plethysmographs which monitor fluctuations in tissue dimensions in deep tissues. The principles of operation and the measured parameters, however, are completely different from the present invention. It will thus be realized that the present invention seems to be unique in its power to monitor the microcirculation dynamics by its viscoelastic-related properties.

The fact that the microcirculatory system responds sensitively to drugs, anaesthetics and emotional stress and that the quantification of such response is a great need in clinical medicine and diagnostics, suggest a variety of applications for the device. Here, its capability of providing a calibrated output is essential. It is worthwhile to mention that the device has been tested in parallel with monitors that constitute a commercial polygraph, among them a finger plethysmograph, a strain gauge plethysmograph and a skin conductivity meter. Tests that have been conducted under different states of emotional stress demonstrated the unique power of the device in monitoring emotional states and their dynamics, and therefore it might be valuable in psychiatry. The correlation between the dynamic patterns displayed by the vasomotion in some diseases suggest that after an appropriate research, the device could be used for early detection of some diseases or as an alarm for dangerous states of the circulation systems as known to occur in diabetes or dehydration. In this respect, it should be mentioned that a telemetrical version of the device can be constructed: The probe and a miniature of the frequency generator will be attached to a person. The output which happens to occur in the FM radio frequencies will be broadcasted. The demodulator and the signal analyser will be placed at another location. In this form the device can save medical personnel. Finally, the telemetrical version can be used for monitoring the psychophysiological states of astronauts and pilots. For these applications, the fact that the device can be worn without any inconvenience and the utilised intensity of the ultrasonic waves is well in the safety region, are crucial.

It will be evident to those skilled in the art that the invention is not limited to the details of the foregoing illustrative embodiments and that the present invention may be embodied in other specific forms without departing from the essential attributes thereof, and it is, therefore, desired that the present embodiments be considered in all respects as illustrative and not restrictive, reference being made to the appended claims, rather than to the foregoing description, and all changes which come with the meaning and range of equivalency of the claims are, therefore, intended to be embraced therein.

What is claimed is:

1. An ultrasonic device for continuously and noninvasively monitoring instantaneous fluctuations in visoelastic-related properties of a tissue, comprising a pair of substantially parallel, spaced-apart piezoelectric transducers having front and rear surfaces and adapted to bracket and, with their respective front surfaces come in direct ultrasonic contact with living tissue inserted in a gap between said front surfaces, said transducers, constituting together with said tissue an oscillating system, at least one of said transducers being adjustable with respect to the other transducer whereby the distance between said transducers is adjustable to enable insertion and clamping of a segment of living tissue therein, further comprising a continuous wave frequency generator producing a wave signal, an input electrode connected at one end thereof to the rear surface of one of said transducers and connected at the other end thereof to a frequency generator, and an output electrode connected at one end thereof to the rear surface of the other one of said transducers, and connectable at the other end thereof via an amplifier and demodulator to a signal analyzer, wherein said wave signal is applied continuously and is subjected, via said living tissue, to multiple reflections between said pair of transducers, and wherein said signal, when demodulated, possesses a frequency-dependent peak structure in which the peaks are located at the resonance frequencies of said oscillating system, the parameters of which peaks are a function of the instantaneous viscoelastic properties of said tissue.

2. The device as claimed in claim 1, wherein said transducers are affixed in a mount, at least one of said transducers being mounted in an insert slidingly held in said mount.

3. A method for continuously and noninvasively monitoring instantaneous fluctuations in viscoelastic-related properties of a tissue with high resolution, comprising the steps of:
providing a pair of substantially parallel, spaced-apart piezoelectric transducers having front and rear surfaces, at least one of said transducers being adjustable with respect to the other transducer;
inserting a segment of living tissue into a gap between said spaced-apart transducers;
adjusting the distance between said transducers so as to bring the front surfaces of both transducers in direct ultrasonic contact with said living tissue to form together with said transducers, an oscillating system;
producing a wave signal by means of a frequency generator connectable to one of said transducers;
continuously applying said wave signal and subjecting it, via said living tissue, to multiple reflections between said pair of transducers at resonance conditions of said oscillating system;
demodulating said signal with the aid of a demodulator, and
analyzing said signal as demodulated to obtain the instantaneous fluctuations in the propagation velocity and/or absorption of said wave signal, being a function of the instantaneous viscoelastic properties of said tissue.

4. An ultrasonic device for continuously and noninvasively monitoring instantaneous fluctuations in viscoelastic-related properties of a tissue, said device comprising:
a first piezoelectric ultrasonic transducer;
a second piezoelectric ultrasonic transducer;
means for mounting said tissue in direct tissue contact with said first and second transducers, said tissue sandwiched between said two transducers, said mounting means further including means for adjusting the position of at least one of said transducers to insure direct tissue contact between said transducers and said tissue, said first transducer, said second transducer and said tissue all comprising an oscillating system;
generator means, connected to said first transducer, for producing a periodic signal; and
analyzer means responsive to a signal received at said second transducer, for demodulating said received signal and for establishing fluctuations in the frequencies at which said oscillating system resonates, and the absorption of said signal at said frequencies, which frequencies and absorptions are functions of the instantaneous viscoelastic properties of said tissue.

5. A method for continuously and noninvasively monitoring instantaneous fluctuations in viscoelastic properties of a tissue, said method comprising the steps of:
providing an oscillating system comprised of said living tissue and two piezoelectric ultrasonic transducers, wherein said tissue is in direct contact with and located between said transducers forming a first transducer/tissue interface and a second transducer/tissue interface;
applying a periodic electrical signal to said first transducer, thereby generating a sound wave at said first transducer/tissue interface;
receiving sound waves at said second transducer/tissue interface and thereby providing an electrical signal at said second transducer;
demodulating said second transducer electrical signal; and
analyzing said demodulated signal to determine the fluctuations in the frequencies at which said oscillating system resonates and the absorption of said signal at said frequencies, which frequencies and absorptions are functions of the instantaneous viscoelastic properties of said tissue.

* * * * *